United States Patent
Huber et al.

(10) Patent No.: US 7,357,575 B2
(45) Date of Patent: Apr. 15, 2008

(54) TELESCOPING TABLE

(75) Inventors: Marc A. Huber, San Jose, CA (US); Paul Hug, Saratoga, CA (US); Timothy T. Buskard, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1 day.

(21) Appl. No.: 10/571,864

(22) PCT Filed: Sep. 9, 2004

(86) PCT No.: PCT/IB2004/051725

§ 371 (c)(1), (2), (4) Date: Mar. 14, 2006

(87) PCT Pub. No.: WO2005/025423

PCT Pub. Date: Mar. 24, 2005

(65) Prior Publication Data

US 2007/0080293 A1    Apr. 12, 2007

Related U.S. Application Data

(60) Provisional application No. 60/503,708, filed on Sep. 17, 2003, provisional application No. 60/513,101, filed on Oct. 21, 2003.

(51) Int. Cl.
*A61B 6/04* (2006.01)
(52) U.S. Cl. .......................... 378/209; 378/20
(58) Field of Classification Search ........ 378/208–209, 378/205, 195, 20, 198; 5/601
See application file for complete search history.

(56) References Cited

U.S. PATENT DOCUMENTS 4,088,888 A    5/1978    Brook et al. ................. 250/445

(Continued)

FOREIGN PATENT DOCUMENTS

WO    WO 02/26137 A1    4/2002

OTHER PUBLICATIONS

General Electric "Proven Impact GE Medical Systems Announces New Nuclear Medicine System" GE Stock Sep. 17, 2003.

(Continued)

*Primary Examiner*—Hoon Song

(57) ABSTRACT

A telescopic table system (32) is used for imaging a subject in at least a first modality (12) and a second modality (14). The first modality is disposed adjacent to the second modality to align a subject receiving bore (24) of the first modality with a subject receiving bore (36) of the second modality. The telescoping table system (32) includes a base (108), an intermediate pallet (78) and a subject pallet (82) on which a subject is loaded prior to imaging. The subject pallet (82) is mounted and supported to retain a constant cantilevering with respect to the intermediate pallet (78) at all longitude positions to prevent deflection changes while extending into any of the imaging modalities. The subject pallet (82) is moved through the first modality subject receiving bore (24) for imaging in the first modality. The subject pallet (82) is withdrawn from the first modality (12) and aligned with the intermediate pallet (78). The intermediate pallet (78) is extended through the first modality subject receiving bore (24) to the intermediate support (118) which is disposed between the first and second modalities. The subject pallet (82) is moved along the intermediate pallet (78) through the second modality subject receiving bore (36) for imaging, while the intermediate pallet is supported by the intermediate support (118).

15 Claims, 5 Drawing Sheets

U.S. PATENT DOCUMENTS

| | | | |
|---|---|---|---|
| 4,131,802 A | 12/1978 | Braden et al. | 250/445 |
| 4,475,072 A | 10/1984 | Schwehr et al. | 318/602 |
| 4,484,571 A | 11/1984 | Velazquez | 128/134 |
| 4,657,235 A | 4/1987 | Schar | 269/322 |
| 4,984,774 A | 1/1991 | Zupancic et al. | 269/322 |
| 5,199,060 A | 3/1993 | Kato | 378/196 |
| 5,490,297 A | 2/1996 | Bradcovich et al. | 5/601 |
| 5,619,763 A | 4/1997 | Randolph et al. | 5/601 |
| 5,866,906 A | 2/1999 | Jensen | 250/363.05 |
| 5,960,054 A * | 9/1999 | Freeman et al. | 378/4 |
| 6,094,760 A | 8/2000 | Nonaka et al. | 5/601 |
| 6,346,706 B1 | 2/2002 | Rogers et al. | 250/363.04 |
| 6,615,428 B1 * | 9/2003 | Pattee | 5/601 |
| 6,961,606 B2 * | 11/2005 | DeSilets et al. | 600/415 |
| 2002/0036268 A1 | 3/2002 | Stark | 250/369 |
| 2002/0104163 A1 | 8/2002 | Reimann | 5/601 |
| 2002/0120986 A1 | 9/2002 | Erbel et al. | 5/601 |
| 2003/0078489 A1 * | 4/2003 | DeSilets et al. | 600/407 |

OTHER PUBLICATIONS

Siemens "Biograph Adds Greatly to the Diagnostic Accuracy of Cancer" www.siemens.com Sep. 17, 2003.

* cited by examiner

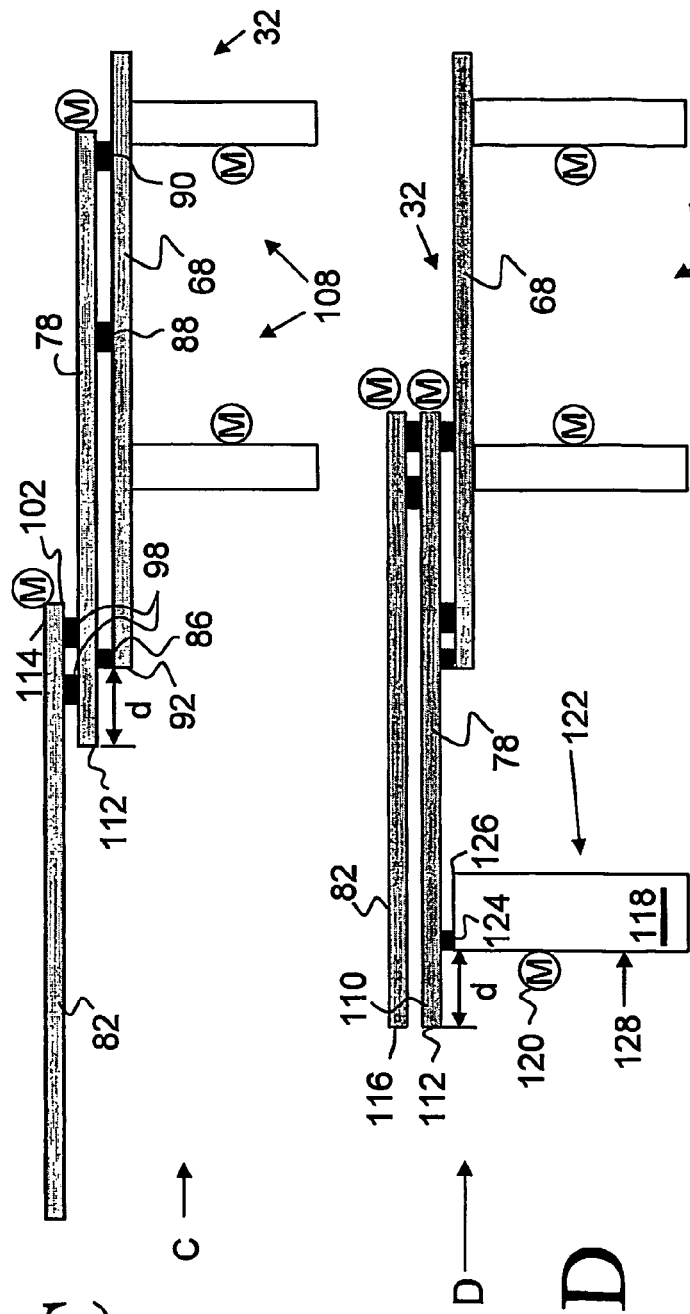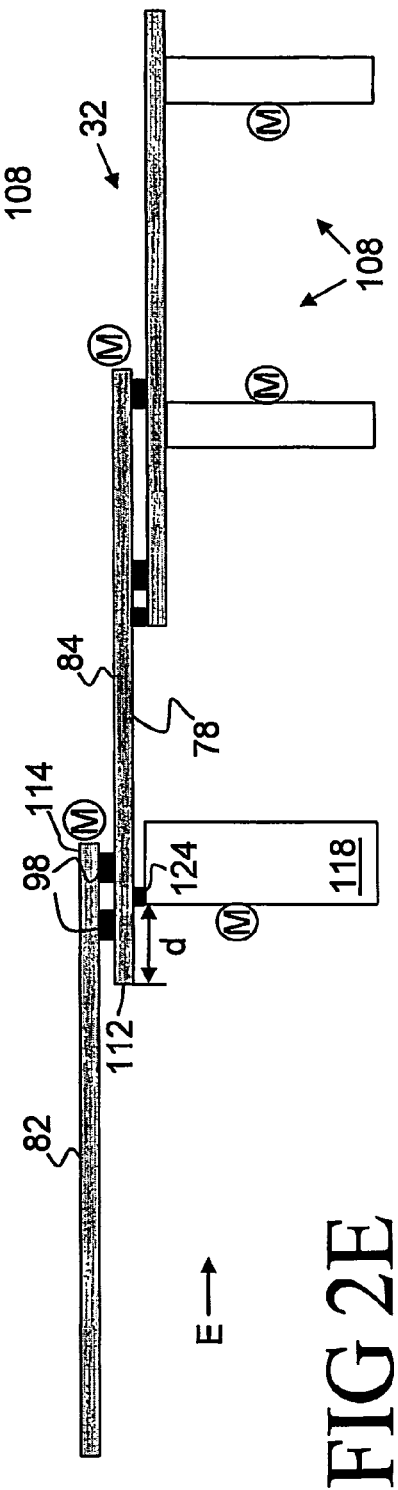

TELESCOPING TABLE

CROSS REFERENCE TO RELATED APPLICATIONS

This application claims the benefit of U.S. provisional application Ser. No. 60/503,708 filed Sep. 17, 2003, and U.S. provisional application Ser. No. 60/513,101 filed Oct. 21, 2003 which are incorporated herein by reference.

The present invention relates to the diagnostic imaging systems and methods. It finds particular application in conjunction with multi-modality systems such as the GEMINI™ PET-CT system manufactured by Philips. It will be appreciated that the invention is also applicable to the combination of SPECT and CT scanners, and the other scanner combinations.

In multi-modality tomographic systems, two or more different imaging modalities are used to locate or measure different constituents in the object space. In the PET-CT system, the PET creates images of high metabolic activity in the body, rather than creating images of surrounding anatomy. CT scans allow doctors to see the internal structures within the human body. Before having a PET-CT scan, the subject receives a dose of a radiopharmaceutical. The pharmaceutical concentrates in the blood, a particular organ, or region and causes radiation to be emitted from this organ or region. During the scan, tracings of the emitted radiation are detected by the system creating an image of the distribution of the radiopharmaceutical in the subject. The image can show the circulatory system and/or the relative absorption of the radiopharmaceutical in various regions or organs. Integration of the anatomical data from the CT scan with the metabolic data from the PET scan in the PET-CT image gives physicians visual information to determine if disease is present, the location and extent of disease and track how rapidly it is spreading as well as relating the PET image to the subject's physiology. The PET-CT system is particularly helpful in difficult-to-treat regions (e.g. head & neck area, mediastinum, postsurgical abdomen) and localization of the treatment area for the subjects receiving radiation therapy or chemotherapy.

The multi-modality imaging requires the subject support table be slidable horizontally into the first and the second modality. Extending the pallet a sufficient distance to span both modalities causes problems either with large table or deflection of subject pallet. Typically, the subject pallet is supported at front and rear ends by support structures. As the pallet starts extending to a fully extended position, its support changes from being supported on two ends to being supported on one end. In the beginning of the motion, the pallet looks as a straight line. As it is extended into the first modality, it is slightly bent. The more the pallet extends, the more it bends, causing different deflection and subject positioning in the second modality compared to the first one and introducing an error in the orientation of detectors with respect to the subject.

There is a need for a subject support table that has a constant deflection during imaging in both modalities with a safe retraction technique, which allows the subject pallet to be retracted in an efficient manner during emergency situations. The present invention provides a new and improved imaging apparatus and method which overcomes the above-referenced problems and others.

In accordance with one aspect of the present invention, a diagnostic imaging system includes a first diagnostic scanner of a first modality having a subject receiving bore. A second diagnostic scanner of a second modality having a subject receiving bore is disposed adjacent the first diagnostic scanner with the second modality subject receiving bore being aligned with the first modality subject receiving bore. An intermediate support is disposed between the first and second diagnostic scanners. A telescoping table system including a base is disposed adjacent the first diagnostic scanner for imaging a subject in at least the first modality and the second modality. An intermediate pallet having a tip and a trailing edge is mounted to the base for longitudinal movement between at least a retracted position and an extended position with the tip extending outward from the base. A subject pallet has bearing supports mounted adjacent subject pallet trailing edge such that the subject pallet is cantilevered therefrom. The bearing supports are mounted to the intermediate pallet for longitudinal movement thereal-ong. The subject pallet moves through the first modality subject receiving bore. The intermediate pallet extends through the first modality subject receiving bore to the intermediate support. The subject pallet moves along the intermediate pallet through the second modality subject receiving bore.

In accordance with another aspect of the present invention, a method is disclosed. An intermediate pallet is movably mounted to a base for longitudinal movement therealong between at least a retracted position and an extended position. A subject pallet having a leading edge and a trailing edge is movably mounted on the intermediate pallet for longitudinal movement therealong with bearing supports mounted adjacent the trailing edge only such that the subject pallet is cantilevered therefrom.

One advantage of the present invention resides in stabilizing deflection of the subject pallet of the telescopic table while fully extending the subject pallet into second modality.

Another advantage of the present invention resides in improving registration in multiple modality systems.

Yet another advantage of the present invention resides in accomplishing safe retraction of the subject pallet in emergency situations.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

FIG. 2C is a diagrammatic illustration of a subject support table with a subject pallet extending into the first modality;

FIG. 2D is a diagrammatic illustration of a subject support table in a second modality start position;

FIG. 2E is a diagrammatic illustration of a subject support table with a subject pallet extending into the second modality;

Figure 1:
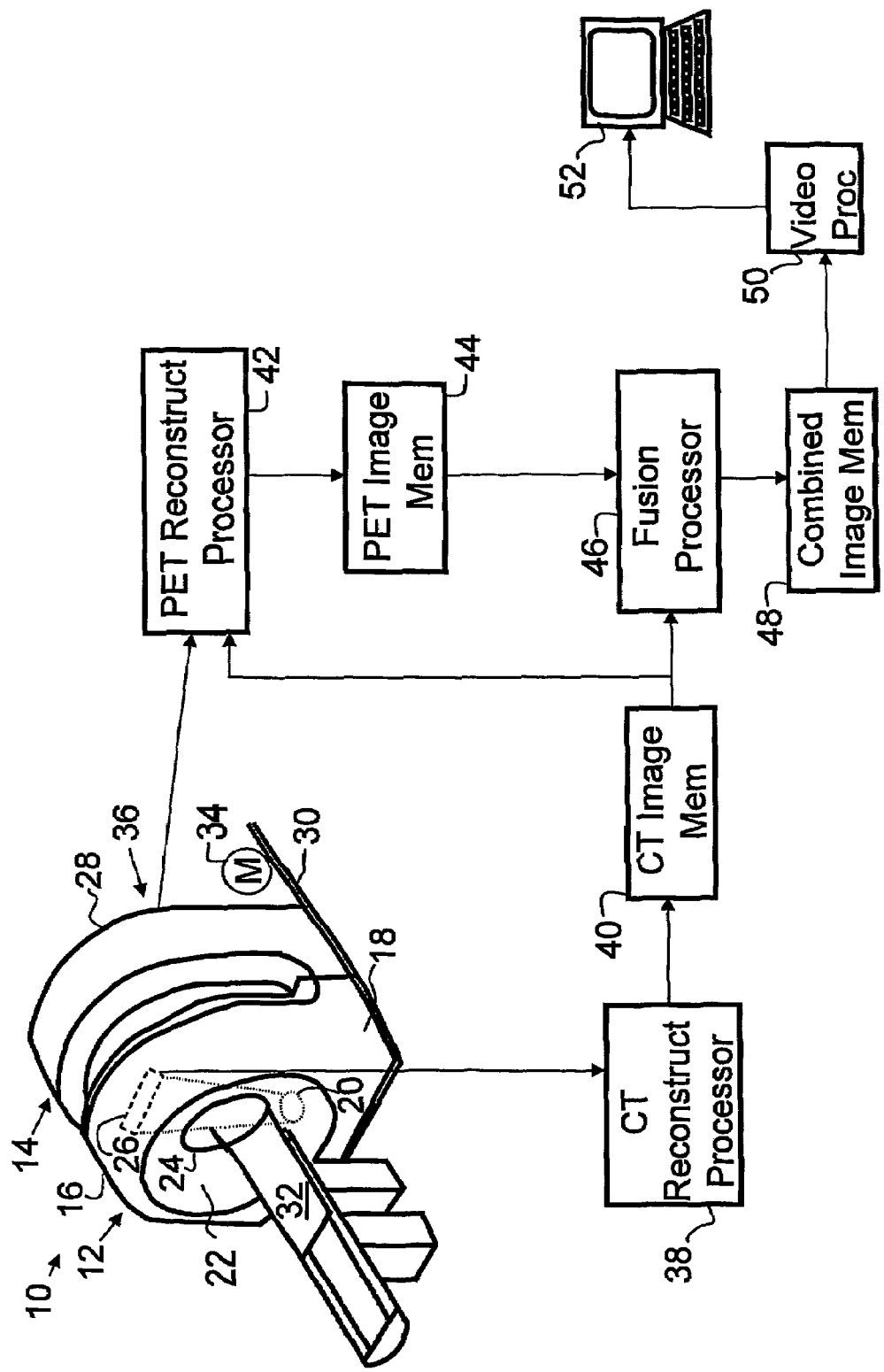
FIG. 1 is a diagrammatic illustration of a CT-PET imaging system.

With reference to FIG. 1, a multi-modality system 10 includes a computed tomography imaging system or a first modality 12 and a nuclear imaging system or a second modality 14. The computed tomography (CT) imaging system 12 includes a CT scanner 16 including a non-rotating gantry 18. An x-ray tube 20 is mounted to a rotating gantry 22. A bore 24 defines a subject receiving bore of the CT scanner 16. An array of radiation detectors 26 is disposed on the rotating gantry 22 to receive radiation from the x-ray tube 20 after the x-rays transverse the subject receiving bore 24. Alternatively, the array of detectors 26 may be mounted on and encircle the non-rotating gantry 18.

The nuclear imaging system 14 preferably includes a positron emission tomography (PET) scanner 28 which is mounted on tracks 30. Of course, SPECT and other nuclear imaging systems are also contemplated. The tracks 30 extend in parallel to a longitudinal axis of a subject support table or couch 32, thus enabling the CT scanner 16 and PET scanner 28 to form a closed system for dual modality use or moved apart for independent operation (not shown). A moving means 34, such as a motor and a drive, is provided to move the scanner 28 between the open and closed positions. Detectors (not shown) are arranged around a bore 36 which is aligned with the CT scanner bore 24 defining a subject receiving bore of PET scanner 28. In the PET system, the detectors are preferably arranged in a stationery ring, although rotatable heads are also contemplated. In the SPECT system, the detectors are preferably incorporated into individual heads, which are mounted for rotational and radial movement relative to the subject.

With continuing reference to FIG. 1, a subject is positioned on the subject support table 32 which is moved to position the subject in the CT scanner subject receiving bore 24, where the CT image is taken. Electronic data is reconstructed into a 3D CT image by a CT reconstruction processor 38 and stored in a CT image memory 40. Next, the subject support table 32 with the subject is moved into the PET receiving bore 36 for a 3D image to be generated by the PET scanner 28. Electronic data is reconstructed into a PET image by a PET reconstruction processor 42 and stored in a PET image memory 44. Optionally, the CT image is used in the nuclear image reconstruction to correct for attenuation due to bones or dense tissue.

A fusion processor or means 46 receives the both CT and PET images to combine the CT and PET image into one 3D image. A combined image is stored in a 3D combined image memory 48. A video processor 50 retrieves the data from the 3D combined image memory 48 and processes the received data for a display on a monitor 52.

Figure 2A:
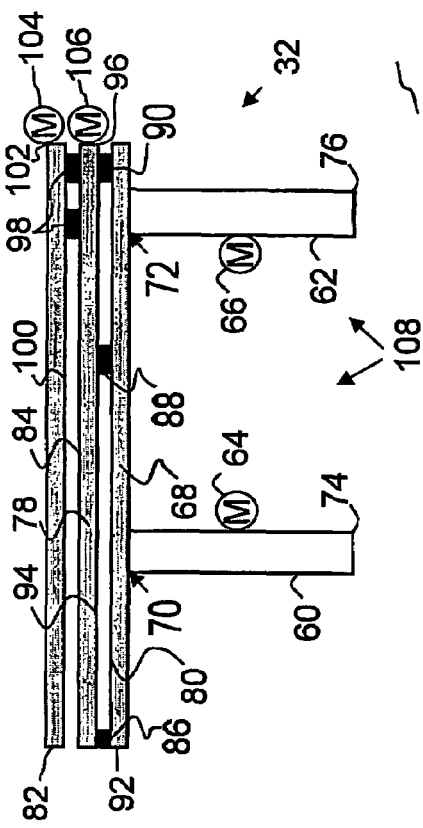
FIG. 2A is a diagrammatic illustration of a subject support table in a retracted position.

With reference to FIG. 2A, the subject support table 32 is shown in a collapsed or fully retracted position A that is typically used to load and unload the subject. The subject support table 32 is floor mounted by a use of two support base members or columns 60, 62, each including drive mechanisis 64, 66 which are used to move the subject support table 32 to a higher and lower positions with respect to the floor. A main support pallet 68 is positioned substantially horizontally on upper ends 70, 72 of the columns 60, 62. Lower ends 74, 76 of the columns 60, 62 are preferably bolted down to secure the subject support table 32 to the floor. The subject support table 32 includes an intermediate pallet 78 which is spaced above an upper surface 80 of the main support pallet 68. A subject pallet 82, fabricated from a radiolucent material, is positioned above an upper surface 84 of the intermediate pallet 78. The subject pallet is preferably a stiffened carbon fiber to minimize and avoid deflection even with the heaviest subjects. The intermediate pallet 78 is supported by a static support member 86, and first and second intermediate bearing support members 88, 90. The static support member 86 is positioned on the main support pallet upper surface 80 about a leading edge 92 of the main support pallet 68, to support a lower surface 94 of the intermediate pallet 78. The first and second intermediate bearing support members 88, 90 are disposed on the intermediate pallet lower surface 94. The second intermediate support member 90 is positioned near a trailing edge 96 of the intermediate pallet 78 for movably supporting the intermediate pallet on the main support pallet upper surface 80.

The subject pallet 82 is mounted in cantilevered fashion by subject pallet bearing support members 98 positioned on a lower surface 100 about a trailing edge 102 of the subject pallet 82 for movably supporting the subject pallet 82 on the intermediate pallet upper surface 84. Motors 104, 106 drive the intermediate pallet 78 and the subject pallet 82 respectively to extend the subject table 32 into the first and second modalities (not shown) for imaging.

Figure 2B:
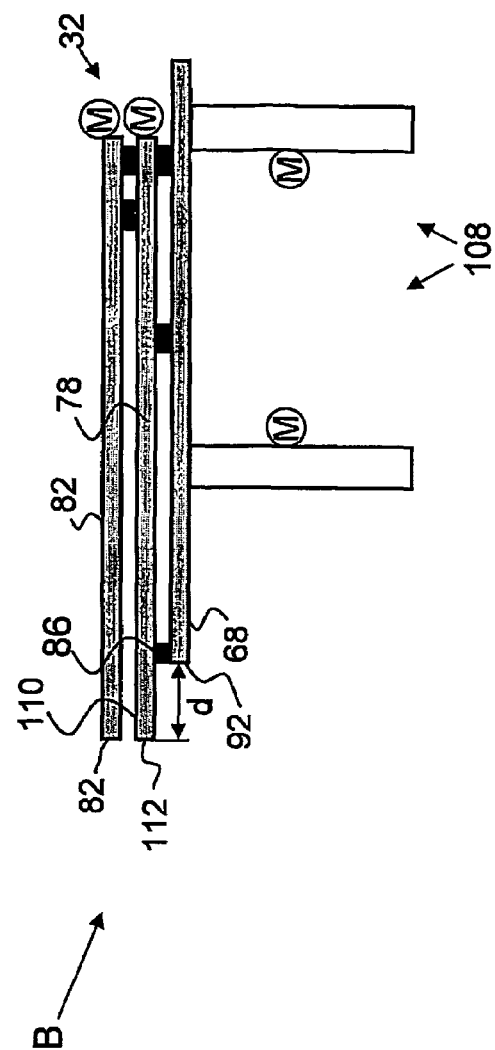
FIG. 2B is a diagrammatic illustration of a subject support table in a first modality start position.

With reference to FIG. 2B, the subject support table 32 is at a position B, in which both intermediate and subject pallets 78, 82 are slightly extended with respect to the main support pallet 68 and arrived at a start position of the first modality (not shown). A tip 110 of the intermediate pallet 78 adjacent to a leading edge 112 of the intermediate pallet 78 is supported by the static support member 86. An offset between the main pallet leading edge 92 and the intermediate pallet leading edge 112 is represented by a distance d which is the distance from the subject support table to the first scanner. At the position B, the subject pallet 82 when loaded with a maximum size subject is substantially parallel to the ground.

With reference to FIG. 2C, the subject support table 32 is at a position C, in which the subject pallet 82 is fully extended into the first modality (not shown). Since the intermediate pallet 78 has not been moved, the tip 110 is still supported by the static support member 86, which is offset from the intermediate pallet leading edge 112 by the same distance as in the position B, e.g. distance d as shown in FIG. 2B, regardless of the degree of extension of the subject pallet into the first modality. An extended subject pallet 82 is supported by the subject pallet bearing support members 98 at a rear end section 114 adjacent to the subject support pallet trailing edge 102 with the same degree of cantilevering. Because the subject pallet is supported cantilevered from the support members 98, the loaded subject pallet 82 has no more or less deflection in position C than in position B. Because the cantilevering does not change as different parts of the subject are positioned in the first scanner, the degree of deflection does not change.

With reference again to FIG. 2B and further reference to FIG. 2D, to image in the second scanner, the subject pallet 82 is withdrawn to the position of FIG. 2B. Then the subject pallet 82 extends together with the intermediate pallet 78 to the position of the subject support table 32 is at a position D. It should be noted that because the subject table bearing blocks 98 are positioned between intermediate support blocks 88, 90, the subject load is at the back of the intermediate pallet 78 as the two pallets move together. There is no subject load on the front end 110 of the intermediate pallet. The subject and intermediate pallets 82, 78 are extended through the first modality (not shown) and arrived at a start position of the second modality (not shown). There is no substantial offset of the intermediate pallet leading edge 112 and a leading edge 116 of the subject pallet 82. A catcher 118 supports the intermediate pallet 78 in the extended position to carry the load that will be placed on the intermediate pallet tip 110 when the subject pallet extends. More particularly, the catcher 118 includes a motor 120 which drives an associated lift mechanism 122 to move the catcher 118 in lower and higher positions with respect to the floor. Typically, in the positions A-C, the catcher 118 is idle and kept in a collapsed position. When the intermediate pallet 78 is fully extended, the motor 120 drives the lift mechanism 122 to extend the catcher 118 until a catcher support member 124, positioned on an upper surface 126 about a leading edge 128 of the catcher 118 touches the intermediate pallet bottom surface 94. Preferably, the intermediate pallet 78 is manufactured from a stiff carbon fiber to prevent deflection and maintain the intermediate pallet substantially flat with respect to the floor.

With continuing reference to FIG. 2D and reference again to FIG. 2C, an offset d between the catcher leading edge 128 and the intermediate pallet leading edge 112 is the same as the offset between the main pallet leading edge 92 and the intermediate pallet leading edge 112 in the position C. In this manner, the intermediate pallet is supported the same in positions C and D.

Figure 3:
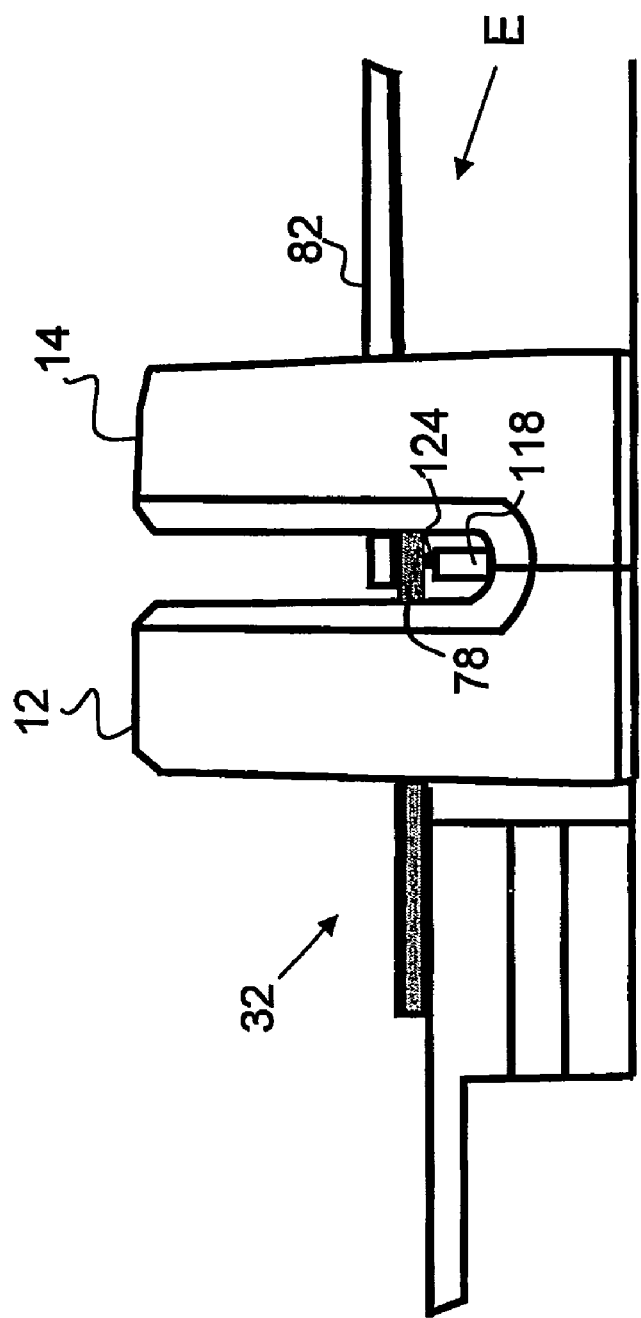
FIG. 3 is a diagrammatic illustration of a PET-CT imaging system with a subject support table extending into the second modality.

With reference to FIGS. 2E and 3, the subject support table 32 is at a position E, in which the subject pallet 82 is fully extended into the second modality 14. Since the intermediate pallet 78 has not been moved, the intermediate pallet tip 110 is still supported by the catcher support member 124 which is offset from the intermediate pallet leading edge 112 by the same distance d as in the positions B-D discussed above. Thus, the intermediate pallet receives the same loading and undergoes the same deflection, if any, in positions C and E. An extended subject pallet 82 is supported by the subject support members 98 at the subject pallet rear end section 114 in the same cantilevered fashion. Due to the cantilever mounting of the subject pallet, there is no change in the deflection of the subject pallet regardless which portion of the subject is positioned in the second scanner.

With continuing reference to FIG. 2E and reference again to FIG. 2C, during imaging in the second modality, the loaded subject pallet 82 is deflected by the same amount, as it was deflected in position C during imaging in the first modality. The constant deflection of the subject pallet 82 in both modalities ensures more reliable registration between the modalities as the subject orientation with respect to the detectors stays consistent.

To retract the subject pallet, the reverse procedure is followed. Specifically, the subject pallet moves from position E to position D. Then, both pallets move together from position D through position B to position A, at which position the subject is unloaded.

Figure 4:
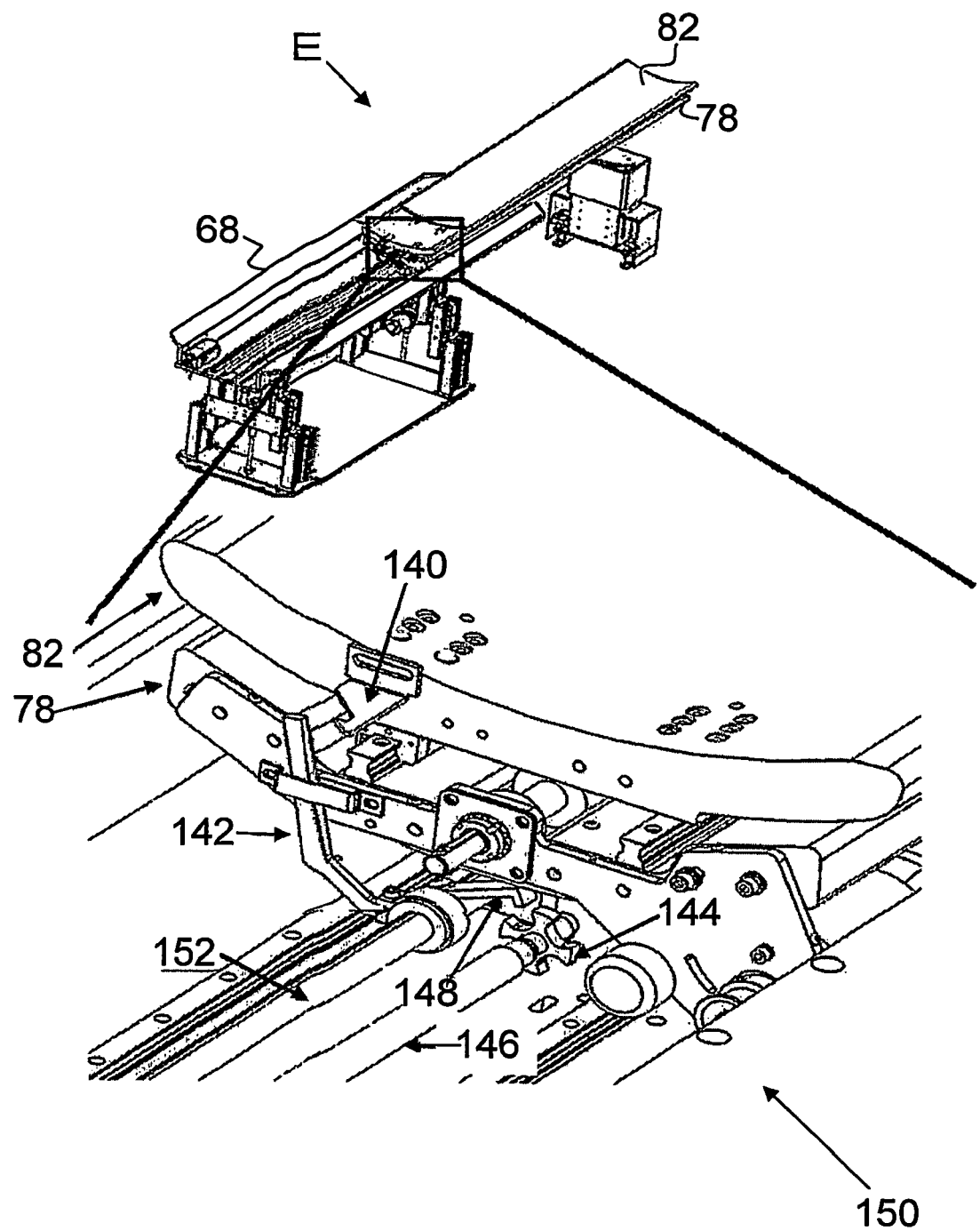
FIG. 4 is a mechanical drawing depicting a portion of a safety release mechanism.

With continuing reference to FIG. 3 and further reference to FIG. 4, during normal operation the electric power is ON. To permit the movement of the pallets 78, 82, a solenoid (not shown) rotates a spline shaft 152 against a spring bias to lift a locking lever 148 out of a sprocket 144 and move shaft lever 142 out of path of latch 140. Lifting the locking lever 148 out of sprocket 144 allows a leadscrew 146 to be turned to move the intermediate pallet 78 between positions B and D. Software ensures that the intermediate pallet 78 cannot be driven if the subject pallet 82 is extended to the positions C and E. A safety release or extraction mechanism 150 ensures that the subject pallet 82 can be retracted manually from the fully extended position E quickly back into the collapsed position A in a safe sequence. The subject pallet 82 is fully retracted before the intermediate pallet 78 is retracted as discussed in greater detail below. During the imaging in the second modality 14, e.g. position E, the intermediate pallet 78 is fully extended and the subject pallet is partially to fully extended. The intermediate pallet 78 is supported by the catcher 118. In an emergency, e.g. when the electric power or computer control is lost, the solenoid (not shown) relaxes allowing the spline shaft 152 to be rotated by a spring bias allowing locking lever 148 to engage sprocket 144 and allows lever 142 to move into the path of latch 140. The attendant pushes or pulls the subject pallet rearward. The interaction of the leadscrew locking lever 148 and the leadscrew sprocket 144 prevents the leadscrew 146 from turning, ensuring that the intermediate pallet 78 cannot move. When the subject pallet 82 is brought to the fully retracted position D by medical personnel, the latch 140 disposed on the subject pallet 82 latches onto a shaft lever 142 locking the subject pallet 82 into the retracted position. When the subject pallet 82 is brought manually substantially to the filly retracted position D, the subject latch 140 includes a ramp that pushes on the shaft lever 142, forcing the shaft 152 to rotate against a spring bias. When the shaft 152 rotates, it disengages the leadscrew locking lever 148 from the leadscrew sprocket 144, unlocking the intermediate pallet leadscrew 146. Once the leadscrew 146 can turn, continued manual rearward pressure moves the intermediate pallet 78 into the retracted position.

Because there is substantially no load on the forward end of the intermediate pallet in position D and because the support block 124 was raised to just touch the underside of the intermediate pallet, the intermediate pallet 78 slides easily off the support block 124, even without lowering the catcher 118. In this manner, an attendant can manually push or pull the subject quickly to the unloading position A in a continuous motion, without computer control and/or electric power. With computer control and electric power present, the pallets can be retracted with motor power.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

Having thus described the preferred embodiments, the invention is now claimed to be:

1. A telescopic table system for imaging a subject in at least a first modality and a second modality, the table comprising:
   a base;
   an intermediate pallet having a tip and a trailing edge mounted to the base for longitudinal movement between at least a retracted position and an extended position with the tip extending outward from the base;
   a subject pallet having a leading edge and a trailing edge; and
   bearing supports mounted adjacent the subject pallet trailing edge such that the subject pallet is cantilevered therefrom, the bearing supports being mounted to the intermediate pallet for longitudinal movement therealong;
   a catcher support member which is disposed on a top surface of an intermediate support; and
   a lift mechanism which raises the intermediate support until the catcher support member comes into contact with an intermediate pallet lower surface to support the intermediate pallet tip.

2. The system as set forth in claim 1, wherein the intermediate support is disposed between the first and second modalities for supporting the tip of the intermediate pallet in the extended position such that the intermediate pallet is supported against deflecting as the subject pallet moves along the intermediate pallet into the second modality.

3. The system as set forth in claim 1, wherein a leading edge of the intermediate pallet is cantilevered a common distance past the catcher support member when the subject pallet extends into the second modality as past the static support member when the subject pallet extends into the first modality.

4. A diagnostic imagine system comprising:
   a first diagnostic scanner of a first modality, the first diagnostic scanner having a subject receiving bore;
   a second diagnostic scanner of a second modality, having a subject receiving bore, the second diagnostic scanner being disposed adjacent the first diagnostic scanner with the second scanner subject receiving bore being aligned with the first scanner subject receiving bore;

an intermediate support disposed between the first and second diagnostic scanners;
a telescoping table system including:
a base disposed adjacent the first diagnostic scanner,
an intermediate pallet having a tip and a trailing edge mounted to the base for longitudinal movement between at least a retracted position and an extended position with the tip extending outward from the base, through the first scanner subject receiving bore to engage the intermediate support adjacent the tip,
a subject pallet having a leading edge and trailing edge mounted to the intermediate pallet for movement therealong between a retracted position and a cantilevered position, and
a drive mechanism for (a) moving the subject pallet through the first scanner subject receiving bore and (b) extending the intermediate pallet through the first scanner subject receiving bore to the intermediate support and moving the subject pallet along the intermediate pallet through the second scanner subject receiving bore.

5. The system as set forth in claim 4, wherein cantilevering of the subject pallet is constant in all longitudinal positions of the subject and intermediate pallets to prevent deflection changes while extending into the first and second scanner subject receiving bores.

6. The system as set forth in claim 4, wherein the base includes a main support pallet including a static support member which supports the tip of the intermediate pallet while the subject pallet extends into the first scanner subject receiving bore during imaging.

7. The table as set forth in claim 4, wherein the subject pallet is manufactured from a stiffened carbon fiber to limit deflection of the subject pallet.

8. The system as set forth in claim 4, further including:
a lift mechanism that lifts the intermediate support into contact with a lower surface of the intermediate pallet to support the intermediate pallet adjacent the tip when the subject pallet is extended into the subject receiving bore of the second scanner.

9. A method of subject handling using a telescopic table system in which an intermediate pallet is movably mounted to a base for longitudinal movement therealong between at least a retracted position and an extended position; and a subject pallet having a leading edge and a trailing edge is movably mounted on the intermediate pallet for longitudinal movement therealong, the method comprising:
loading a subject on the subject pallet while the subject pallet is being supported by the intermediate pallet in the retracted position, and while the intermediate pallet is supported by a static main support member;
while continuing to support the intermediate pallet on the main support member, moving the subject support pallet along the intermediate pallet into a first modality scanner for imaging;
withdrawing the subject support pallet from the first modality scanner to align with the intermediate pallet;
extending the aligned intermediate and subject pallets simultaneously through the first modality scanner to an intermediate support, which includes a catcher support member disposed on a top surface of the intermediate support;
raising a lift mechanism of the intermediate support until the catcher support member comes into contact with an intermediate pallet lower surface to support the intermediate pallet; and
while supporting the intermediate pallet with the catcher support member, moving the subject pallet along the intermediate pallet through a second modality scanner for imaging.

10. The method as set forth in claim 9, wherein a leading edge of the intermediate pallet is cantilevered a common distance past the catcher support member when the subject pallet extends into the second modality scanner as past the static support member when the subject pallet extends into the first modality scanner.

11. The method as set forth in claim 9, further including:
retracting the subject pallet, which is loaded with the subject, from the second modality scanner into the retracted position in an emergency, including the steps of:
(a) locking the intermediate pallet against moving;
(b) retracting the subject pallet from the second modality scanner;
(c) locking the subject pallet into a retracted position in which the subject and intermediate pallets are substantially aligned;
(d) unlocking the intermediate pallet; and
(e) moving the locked and aligned subject and intermediate pallets through the first modality scanner into the retracted position.

12. A medical imaging system comprising:
a first imaging system;
a second imaging system;
a catcher disposed between the first and second imaging systems; and
a common patient support table, wherein the patient support table is movable between a first position where an object to be imaged is within an imaging region of the first imaging system and a second position where the table is supported on the catcher and the object is positioned within an imaging region of the second imaging system;
wherein said common patient support table is cantilevered in both the first position and the second position such that an axial deflection of the patient support table in the first position is the same as an axial deflection of the patient support table in the second position;
wherein the patient support table includes a main support pallet, an intermediate support pallet and a patient support pallet and the intermediate support pallet and the patient support pallet extend from the main support pallet when the patient support table is in the first position, and wherein the patient support pallet extends from the intermediate support pallet and the intermediate support pallet is supported on the catcher when the patient support table is in the second position.

13. The medical system of claim 12, wherein one or more support members are positioned between the patient support pallet and the intermediate pallet such that when the patient support pallet extends from the intermediate pallet, the patient support pallet is cantilevered on the intermediate pallet.

14. The medical system of claim 12 further including:
a lift mechanism that raises and lowers the catcher.

15. The medical system of claim 12, wherein said common patient support table is cantilevered in both the first position and the second position such that an axial deflection of the patient support table in the first position is the same as an axial deflection of the patient support table in the second position.

* * * * *